(12) United States Patent
Sussman et al.

(10) Patent No.: US 9,206,473 B2
(45) Date of Patent: Dec. 8, 2015

(54) METHODS FOR RAPID PRODUCTION OF DOUBLE-STRANDED TARGET DNA

(75) Inventors: Michael R. Sussman, Madison, WI (US); Kathryn E. Richmond, Madison, WI (US); Matt J. Rodesch, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 131 days.

(21) Appl. No.: 13/286,932

(22) Filed: Nov. 1, 2011

(65) Prior Publication Data

US 2015/0284767 A1    Oct. 8, 2015

Related U.S. Application Data

(63) Continuation of application No. 11/148,401, filed on Jun. 8, 2005, now abandoned.

(51) Int. Cl.
   *C12Q 1/68* (2006.01)
(52) U.S. Cl.
   CPC ..................................... *C12Q 1/686* (2013.01)
(58) Field of Classification Search
   None
   See application file for complete search history.

(56) References Cited

U.S. PATENT DOCUMENTS

| 6,117,679 | A * | 9/2000 | Stemmer | 506/1 |
| 6,586,211 | B1 | 7/2003 | Stahler et al. | |
| 6,670,127 | B2 | 12/2003 | Evans | |
| 6,815,167 | B2 * | 11/2004 | Crothers et al. | 435/6.15 |
| 7,135,310 | B2 * | 11/2006 | Bradbury et al. | 435/91.1 |
| 2003/0189110 | A1 | 10/2003 | Kurihara et al. | |
| 2005/0287585 | A1 | 12/2005 | Oleinikov | |

FOREIGN PATENT DOCUMENTS

| EP | 1153127 | 7/2006 |
| WO | 9942813 | 8/1999 |
| WO | 02095073 | 11/2002 |
| WO | 2005089110 | 9/2005 |

OTHER PUBLICATIONS

Higgins et al., The nicking endonuclease N.BstNBI is closely related to Type Iis restriction endonucleases MlyI and PleI , 2001, vol. 29, No. 12, pp. 2492-2501.*
Higgins et al., The nicking endonuclease N.BstNBI is closely related to Type Iis restriction endonucleases MlyI and PleI , 2001, Nucleic Acids Research, vol. 29, No. 12, pp. 2492-2501.*
Udit et al. (Methods in Molecular, 2003, vol. 231:Directed Evolution Library Creation: Methods and Protocols, p. 153-163).*
Schuelke, M. (Nature Biotech., 2000, vol. 18, p. 233-234).*
Horton et al. (Biotechniques, 1990, vol. 8, No. 5, p. 528-535).*
Prodromou, et al., "Recursve PCR: a novel technique for total gene synthesis", Protein Engineering 5:827-829 (1992).
Soderlind, et al., "Domain libraries:Synthetic diversity for de novo design of antibody V-regions", Gene 160:269-272 (1995).
Stemmer, et al. "Single-step assembly of a gene and entire plasmid from large number of oligodeoxyribonucleotides", Gene 164:49-53 (1995).

* cited by examiner

*Primary Examiner* — Stephanie K Mummert
(74) *Attorney, Agent, or Firm* — Quarles & Brady LLP

(57) ABSTRACT

A method of rapidly producing a double-stranded target DNA is disclosed. The method includes the step of producing multiple single stranded primary DNA constructs having (a) partially overlapping and complementary internal regions that together define the target DNA, and (b) flanking regions on either side of the internal regions containing a PCR primer recognition site and a restriction enzyme recognition site. The primary DNA constructs are amplified to form a pool of double-stranded primary constructs, and a restriction enzyme is used to cleave off the flanking regions. The target double-stranded DNA is then assembled from the cleaved fragments. Hundreds of thousands of oligonucleotides can be synthesized and quickly and efficiently assembled into many different individual double-stranded DNA target sequences using this method.

16 Claims, 1 Drawing Sheet

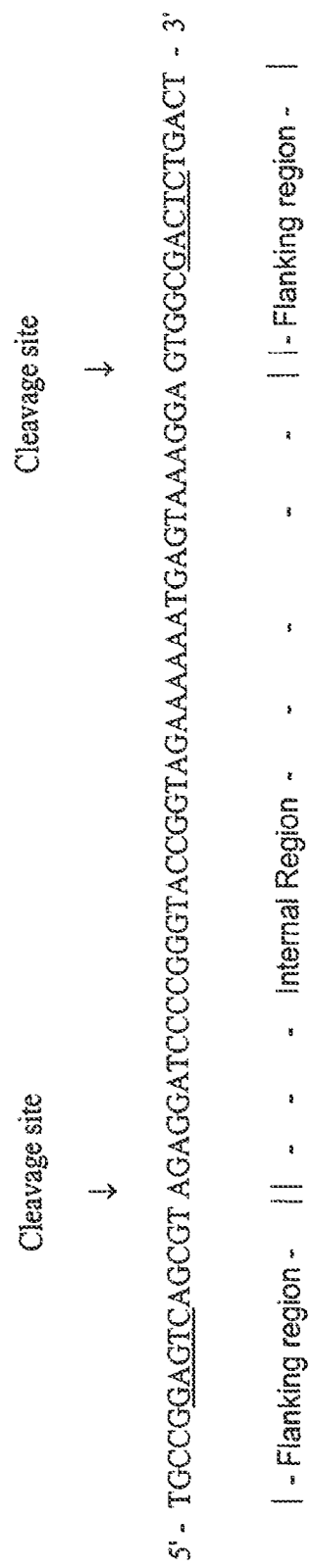

SEQUENCE LISTING

```
<160> NUMBER OF SEQ ID NOS: 5

<210> SEQ ID NO 1
<211> LENGTH: 10
<212> TYPE: DNA
<213> ORGANISM: Artificial
<220> FEATURE:
<223> OTHER INFORMATION: Synthetic Oligonucleotides
```

```
<220> FEATURE:
<221> NAME/KEY: misc_feature
<222> LOCATION: (6)..(10)
<223> OTHER INFORMATION: n is a, c, g, or t

<400> SEQUENCE: 1 gagtcnnnnn                                                            10

<210> SEQ ID NO 2
<211> LENGTH: 70
<212> TYPE: DNA
<213> ORGANISM: Artificial
<220> FEATURE:
<223> OTHER INFORMATION: Synthetic Oligonucleotides

<400> SEQUENCE: 2
tgccggagtc agcgtagagg atccccgggt accggtagaa aaaatgagta aaggagtggc     60
gactctgact                                                           70

<210> SEQ ID NO 3
<211> LENGTH: 70
<212> TYPE: DNA
<213> ORGANISM: Artificial
<220> FEATURE:
<223> OTHER INFORMATION: Synthetic Oligonucleotides

<400> SEQUENCE: 3
tgccggagtc agcgtgaaga acttttcact ggagttgtcc caattcttgt tgaatgtggc     60
gactctgact                                                           70

<210> SEQ ID NO 4
<211> LENGTH: 70
<212> TYPE: DNA
<213> ORGANISM: Artificial
<220> FEATURE:
<223> OTHER INFORMATION: Synthetic Oligonucleotides

<400> SEQUENCE: 4
tgccggagtc agcgtcccgt taacatcacc atctaattca acaagaattg ggacagtggc     60
gactctgact                                                           70

<210> SEQ ID NO 5
<211> LENGTH: 70
<212> TYPE: DNA
<213> ORGANISM: Artificial
<220> FEATURE:
<223> OTHER INFORMATION: Synthetic Oligonucleotides

<400> SEQUENCE: 5
tgccggagtc agcgtactcc agtgaaaagt tcttctcctt tactcatttt ttctagtggc     60
gactctgact                                                           70
```

METHODS FOR RAPID PRODUCTION OF DOUBLE-STRANDED TARGET DNA

CROSS-REFERENCE TO RELATED APPLICATIONS

This application is a continuation of U.S. patent application Ser. No. 11/148,401, filed Jun. 8, 2005, now abandoned which is incorporated herein by reference in its entirety.

STATEMENT REGARDING FEDERALLY SPONSORED RESEARCH OR DEVELOPMENT

This invention was made with government support under DAAD19-02-2-0026 awarded by DOD/DARPA. The government has certain rights in the invention.

BACKGROUND OF THE INVENTION

The invention pertains to the field of molecular biology and techniques and apparatus for the manufacture of DNA molecules of defined or desired sequences. The er vivo manufacture of DNA molecules makes possible the use of those DNA molecules in vivo to synthesize any desired peptides, proteins or assemblies of proteins or combinations of nucleic acids, as may be desired, and to perform a large variety of genetic experiments in living organisms.

In modern biotechnology it is common to create DNA sequences chemically, that is to say apart from any living organism. The DNA sequences are assembled and replicated in vitro using cell free techniques and ultimately are recombined or reassembled into DNA sequences which can be inserted into organisms for biological purposes. It has become commonplace to synthesize short DNA sequences, referred to as oligonucleotides, directly from individual nucleosides and to construct larger DNA sequences from smaller oligonucleotides.

It has also been proposed that one may create larger DNA molecules by the making many smaller, but properly designed, DNA molecules in parallel, and then permitting those smaller molecules, or fragments, to self-assemble and thereby make a longer oligonucleotide. This can be done most conveniently by using a maskless array synthesizer (MAS) instrument, of the type disclosed in published PCT application WO 99/42813 to create a number of single stranded DNA sequences in a massively parallel synthesis operation. The single stranded DNA sequences thus created can then be cleaved from the substrate upon which they are constructed and permitted to anneal and form much larger DNA segments. This process and the general principles behind its operation are described in published PCT application PCT/US02/15951, the disclosure of which is incorporated herein by reference. A unique attribute of the MAS instrument of particular interest for this process is that fact that the instrument can create microarrays in which the oligonucleotides attach in the array are quite long, as long as 60 to 100 nucleotides. It is believed that only this style of microarray instrument permits the synthesis of oligonucleotides of this length in a microarray.

While these methods permit the synthesis of long DNA segments, using the massively parallel synthesis capabilities of the MAS style of instrument, there is one drawback to the methodology described in the aforementioned published PCT applications. The amount of DNA assembled by this synthesis, without other procedures, is relatively small. While the amount of DNA is so small as to be difficult to measure physically, it is believed that approximately 20 picomoles of DNA are synthesized on a typical DNA microarray made by an MAS instrument. The fact that the amount of DNA is this small makes the physical handling and amplification of the DNA a relatively sophisticated procedure. The DNA is so small an amount that if the DNA is handled at a concentration consistent with most DNA reaction conditions, the volume becomes much smaller than the volumes suitable for handling in most fluid handling operations. Conversely, if the solution is diluted to a reasonable volume, then the DNA molecules are so dilute in the solution that the normal enzymes and other agents used for altering and manipulating DNA are difficult to use because of the dilution of the DNA. Accordingly, the process for the massive parallel synthesis of DNA fragments would be improved if methodologies existed to dramatically increase the amount of DNA which is the product of such a process.

BRIEF SUMMARY OF THE INVENTION

The present invention is summarized in a method for making a target DNA sequence in which the method starts with the step of synthesizing in parallel a large number of single stranded DNA primary constructs, each primary construct including an internal region and flanking regions on each side of the internal region, each of the flanking regions including a recognition site for a restriction enzyme which would cut the primary construct at each of the junctions of the internal region and the flanking regions. The next step is amplifying the primary constructs by conducting a PCR reaction on the primary constructs using primers located in the flanking regions of the primary constructs to create an amplified pool of primary constructs. The next step is to digest the amplified pool of primary constructs with a restriction enzyme to cleave the internal regions in the pool of amplified constructs from the flanking regions. Finally, assembly of the target sequence is performed by adding a polymerase and dNTPs to the product of the last step and conducting repetitive denaturing, annealing and extension procedures to assemble the target sequence from the products of the extension.

It is an object of the present invention to improve the process of the synthesis of DNA sequences specifically by massively parallel chemical synthesis of small segments followed by assembly of the small segments into larger DNA sequences.

It is an advantage of the method of the present invention in that it permits amplification of the number of copies of DNA synthesized to increase the amount of DNA available for DNA assemble procedures.

Other objects advantages and features of the present invention will become apparent from the following specification.

BRIEF DESCRIPTION OF THE SEVERAL VIEWS OF THE DRAWINGS

FIG. 1 illustrates a DNA sequence of a potential primary construct for use in the present invention.

DETAILED DESCRIPTION OF THE INVENTION

The present invention is directed toward a method for increasing the yield of oligonucleotides constructed in a massively parallel DNA synthesis operation. The method is best used with a single stranded DNA parallel synthesis technology which permits the synthesis of relatively long oligonucleotides, here called primary constructs. The primary constructs are single stranded DNA molecules, longer than the typical oligonucleotides made on a microarray, being typically on the order of 70 mers or longer. To understand the concept of the present invention, the generalized arrangement of the primary construct is illustrated in FIG. 1, with an exemplary but arbitrary DNA sequence. Each primary construct is composed of an internal region, shown to be a 40 mer in FIG. 1, and two flanking regions, each illustrated as a 15 mer in FIG. 1. The internal region of the primary construct is a sequence of DNA intended to be incorporated in the target DNA sequence being constructed. The flanking regions are regions intended to be functional in the primary sequence and include both PCR primer sites and restriction enzyme recognition sites, so that the primary constructs can be amplified followed by cleavage of the flanking regions, as will be described in more detail below. A core idea of this process is that following detachment of the primary constructs from the substrate, creating a mix pool of single stranded primary constructs, a PCR reaction is run using primers which recognize primer regions in the flanking regions on all of the primary constructs. This amplifies the copy number of each of the numerous primary constructs in parallel. Then the amplified primary constructs are all digested with a restriction enzyme, to cleave off the flanking regions. At this point the internal regions, the 40 mers, are released, independent and can be used in the assembly of the target DNA.

To facilitate comprehension of the process described here, the consistent use of common terminology here is appropriate. In this document, the "target sequence" refers to the ultimate DNA construct, the synthesis of which is the object of the entire process here. The "automated gene synthesizer" or "AGS" instrument refers to an instrument capable of making many different oligonucleotides in parallel, typically, but not necessarily, on a common substrate. The "primary construct" refers to the single stranded oligonucleotides created by the automated gene synthesizer instrument and then released into solution. The "internal region" and the "flanking region" are regions of the primary construct, as illustrated here. The assembly process refers to the methodology used to assemble the internal regions into the target sequence.

The process of constructing the target sequence begins with an automated gene synthesis instrument. This instrument is a device intended to chemically synthesize a large number of single stranded DNA molecules in a massively parallel DNA synthesis process. Any of the commercially used DNA microarray synthesis instruments in use today that can create long pieces of single stranded DNA (greater than 60 mers) may be adapted for this purpose. DNA microarray are available commercially and can be custom made by companies in that business. However, the preferred approach is to use an instrument of the style described in, among other places, U.S. Pat. No. 6,375,903, the disclosure of which is incorporated herein by reference. This style of instrument, originally designed to make DNA microarrays, uses a micromirror device under computer control to make individually customizable and unique microarrays. The instrument and the chemistry used with it can be optimized such that the manufacture of single stranded oligonucleotides is so efficient, that this style of instrument can make 786,000 different oligonucleotides, each up to or over 100 nucleotides in length, in parallel and all in a matter of a few hours. Each manufacture of a microarray is unique and customized, since it is under computer control. The instrument permits the manufacture of multiple microarrays per day, each individually designed and customized. This is the technology that has been adopted to be used as the automated gene synthesizer instrument for the process described here. The microarray synthesized by such an instrument results in many individual groups of similar single stranded oligonucleotides secured on a common substrate. To use the oligonucleotides as the primary constructs in the process here, the oligonucleotides are separated from the substrate, thus making the primary constructs used in this process free in solution. This separation from the substrate can be done by simply using a base or acid labile linkage between the oligonucleotide and the substrate, and then using a base or an acid to release the primary constructs.

Returning to a description of the overall process, the primary constructs are synthesized in parallel using an automated gene synthesis instrument, and the primary constructs are then cleaved from the substrate. As briefly described above, the primary constructs have particular properties. Each of the primary constructs created includes at its opposing ends two flanking regions and has, in its interior, an internal sequence. The sequence of the internal sequence is determined by the sequence of the target DNA, the DNA construct to be made by this overall process. The internal sequences serve the function of the sequences referred to as DNA molecule segments in the disclosure of PCT/US02/15951, incorporated by reference above. Thus each internal region makes up a portion of the total target sequence, and each internal region is complementary to portions of two other internal regions on other primary constructs. The flanking regions have their sequences designed with two important properties in mind. One is that the flanking regions incorporate primer recognition sites for PCR primers. The other is that the flanking regions incorporate a cleavage recognition site for a type II restriction enzyme, that is to say a restriction enzyme that will cut a DNA sequence at a cleavage site that is not its recognition site. This is illustrated again in FIG. 1. Note that the exemplary primary construct of FIG. 1 includes in each flanking region the sequence GAGTC. This is the recognition site for the restriction enzyme Mly I. The site of cleavage of the restriction enzyme Mly I is also indicated in FIG. 1, and note that this site is several bases distant from the recognition site. This same concept may be used with any restriction enzyme that cleaves DNA at a site adjacent to, but not within, the recognition site of the enzyme. Mly I is preferred because its cleavage of double stranded DNA results in a blunt end.

So, again, the process begins with the synthesis of the primary construct on the automated gene synthesizer instrument and the release of the primary constructs from the substrate. At this point, there is a solution of single stranded DNA molecules, but a small number of molecules are made. The next step in the process is to perform a polymerase chain reaction (PCR) DNA amplification reaction. The procedures for conducting PCR reactions are well known in the art. The primers used for the PCR amplification are selected to bind to the primer recognition sites in the flanking regions of the primary constructs. The PCR reaction is conducted for several rounds to thus amplify the number of copies of the primary constructs to whatever magnitude of copies is convenient for the remainder of the process. Since the flanking regions on all of the primary constructs are the same, all of the primary constructs will be amplified in about the same proportion. This idea is subject to a variation, It is envisioned that one alternative is for all the PCR primers and recognition sites to be the same for all the primary constructs so that there is a single amplification of all of the pooled primary constructs recovered from the substrate. Another alternative is to have sets or groups of PCR primers and recognition sites to permit selective amplification of subsets or groups of primary constructs by simply using the PCR primers which target that particular subset or group. The amplified constructs can then be assembled, as described below, followed by amplification of other subsets or groups using different primers.

As might be surmised at this point, after the amplification step, the next step in the process is to cleave the flanking regions from the primary constructs using the restriction enzyme. The entire pool of amplified primary constructs can be digested together to completion. Again it is preferred that a type II restriction enzyme which cuts DNA at a site different from the recognition site is preferred. Referring to the example in FIG. 1, the Mly I enzyme recognizes the motif GAGTC in the flanking region and cuts the molecule five bases displaced from the C base of the recognition site. The use of Mly I is preferred since it leaves a blunt end after cleavage. This cleanly cuts the entire flanking region off of the primary construct leaving only the internal region. Many other suitable restriction enzymes can be used, including BciVI, BmrI, FauI, BsrDI, AlwI and PleI, although these molecule may leave overhanging bases that must either be cleaved off or matched with a complement, depending on whether the overhang is intended to be in the internal region or the flanking region. The result of this step is a pool of DNA segments, each the size of the internal regions. The pool contains multiple copies of each internal region which was represented in the initial pool or primary constructs.

Note that since use of the MAS or AGS instrument permits the sequence of the oligonucleotides it constructs to be completely variable. Hence, the sequence of each of the internal regions in completely selectable and can be precisely defined by the user before the process starts. The pool of constructs now created thus consists of an amplified pool of internal regions composed of sequences selected by the user for assembly into the target sequence.

Once the internal regions are cut from the flanking region, the cut pieces can separated, which can be done by any of several DNA separation techniques. However, as will become apparent from the examples below, it is not always necessary to perform any separation at this stage. Instead, the now independent internal regions can begin the assembly process. As in the process described in PCT/US02/15951, the DNA sequences of the internal regions are each complementary to sequences in the internal regions of other species in the pool. However, in contrast to the situation in the published PCT application, the assembly process starts from here with a pool of double stranded, not single stranded, DNA molecules. So in the method described here, it is preferred that the assembly process be aided by a series of denaturing, annealing and extension steps, with a DNA polymerase in the reaction. In other words, the process is like a PCR reaction, but without any new primers added, so that no amplification occurs. Consider what happens in each annealing and extension step. As the internal regions find their complements, some 40 mer internal regions will match to their exact 40 mer complements, but then the double stranded DNA molecule created by that annealing will not be affected by the DNA polymerase. Other internal regions will hybridize to a different internal region that overlaps the first internal region only in part, i.e. the first step in assembly of the target sequence. When that occurs, the complex thus created is partially double stranded and partially single stranded, and the DNA polymerase will add complements to both single strands to their end. In the example of an internal region with is a 40 mer, and which overlaps another 40 mer by 20 bases, the two hybridized strands would each have their strands extended to create double stranded 60 mers. This process can then be repeated over and over, and in the process longer and longer assembled molecules result, eventually resulting in the full length target molecule. The largest molecule created by this process will be the desired proper target sequence.

One might wonder why the flanking regions include PCR primer sites. One can purchase kits for generalized PCR primers which are intended to amplify all DNA. However, this method is subject to PCR bias, in which some sequences may amplify better than others. By using a common PCR primer in all the flanking regions which are amplified in a common reaction, the possibility of bias in the amplification process is minimized. Bias is also reduced by having all the internal region sequences being of the same length (e.g. 40 base pairs) even though they differ in sequence.

EXAMPLES

Synthesis of Primary Constructs

The Automated Gene Synthesizer (AGS-1) was used to make a chip containing two 60 mer oligonucleotides on a base-labile linker. The primary construct oligonucleotides were designed for amplification and subsequent gene assembly and consisted of (2) flanking 15 mer primer sites containing restriction sites (Mly I; GAGTC(N)5); SEQ ID NO: 1) and internal 30 mer fragments to be used for subsequent gene assembly.

After production, the primary construct oligonucleotides were cleaved off the microarray by treatment of the entire microarray with $NH_4OH$ for 30 minutes. The resulting solution was then removed from the substrate of the microarray, transferred to a tube and left for sixteen hours to allow for removal of base protecting groups. The solution was then dried down in a speed vacuum centrifuge and the precipitate was subsequently resuspended in 5 µl sterile Milli-Q water.

The microarray eluate aliquot (0.2 µl) was used for PCR amplification using two 15 mer PCR primers containing the restriction enzyme site (Mly I) and in the presence of Pfu polymerase. The product of amplification was labeled with 32P using T4 polynucleotide kinase and analyzed by gel electrophoresis on a 1×TBE 20% PAGE Urea gel. After electrophoresis at 1500V for one hour, the gel was placed in a phosphoimager cassette and scanned using the STORM Molecular Dynamics system. The results demonstrated recovery of the intended DNA.

This same process was successfully repeated as noted above except using a monohydroxysilane slide and its treatment with $NH_4OH$ for 60 minutes to cleave oligonucleotides off its surface. This was done to demonstrate that this process is successful on multiple types of surfaces.

Synthesis and Assembly of 100 bp Sequence.

The Automated Gene Synthesizer (AGS-1) was used to make a chip containing four 70 mer oligonucleotides on a base-labile linker. Again, the primary construct oligonucleotides were designed for amplification and subsequent gene assembly and consisted of (2) flanking 15 mer primer sites containing restriction sites (Mly I; GAGTC(N)5 SEQ ID NO: 1) and internal 40 mer fragments to be used for subsequent gene assembly. The sequences of the four primary constructs were as follows:

(SEQ ID NO: 2)
5'TGCCG<u>GAGTC</u>AGCGTagaggatccccgggtaccggtagaaaaaatgagtaaaggaGTGGC<u>GAC</u>

<u>TC</u>TGACT 3' 70 mer - 40F1a (SEQ ID NO: 3)
5'TGCCG<u>GAGTC</u>AGCGTgaagaactatcactggagttgtcccaattcttgttgaatGTGGC<u>GACTC</u>T GACT 3' 70 mer - 40F2a -continued (SEQ ID NO: 4)
5' TGCCGGAGTCAGCGTcccGttaacatcaccatctaattcaacaagaattgggacaGTGGCGACTC TGACT 3' 70 mer - 40Rev9a (SEQ ID NO: 5)
5' TGCCGGAGTCAGCGTactccagtgaaaagttcttcctttactcattttttctaGTGGCGACTCTG ACT 3' 70 mer - 40Rev9b In the sequences presented above, the internal regions are in lower case while the flanking regions are in upper case. The recognition sites for Mly I are underlined. The cleavage site for Mly I is between the upper and lower case letters. Note that the flanking regions are identical in each of the primary constructs. Note also that the 3' half of the internal region in 40F1a is complementary to the 3' half of the internal region of 40Rev9b. The 5' half of the internal region 40Rev9b is complementary to the 5' half of the internal region 40Rev9a, and the 3' half of the internal region of 49Rev9a is complementary to the 3' half of the internal region of 40F2a. The 5' end of the internal regions of 40F1a and 40Rev9a are unmatched.

After production on a microarray, the primary construct oligonucleotides were cleaved off the substrate of the microarray by treatment with $NH_4OH$ for 30 minutes. The solution was then removed from the microarray, transferred to a tube and left for sixteen hours to allow for removal of base protecting groups. The eluate was then dried down in a speed vacuum centrifuge and the precipitate was subsequently resuspended in 5 μl sterile Milli-Q water and used for gene assembly.

A chip eluate aliquot (0.2 μl) was used for PCR amplification, with two 15 mer PCR primers containing the restriction enzyme site (Mly I). After PCR amplification, the product was digested overnight with the restriction endonuclease Mly I to remove all of the flanking regions on all of the DNA strands, leaving multiple copies of the four 40 mer internal regions. The unpurified restriction enzyme digest fragments were then used for subsequent gene assembly and amplification reactions.

Initial target sequence assembly was performed by combining a fraction of the digested PCR product and Pfu polymerase, buffers, and dNTPs in a reaction and cycling to denature, anneal and extend the gene fragments. The assembled sequence was then amplified by PCR with Pfu polymerase, labeled with $^{32}P$ using T4 polynucleotide kinase and analyzed by gel electrophoresis on a 1×TBE 20% PAGE Urea gel. After electrophoresis at 1500V for one hour, the gel was placed in a phosphoimager cassette and scanned using the STORM Molecular Dynamics system. Noted on the gel was the assembly of a 100 bp DNA fragment. This fragment could only be the target sequence resulting from assembly of the internal regions and extension with the polymerase.

Synthesis and Assemble of 180 bp Sequence.

The Automated Gene Synthesizer (AGS-1) was used to make a chip containing eight different 70 mer oligonucleotide primary constructs on a monohydroxysilane slide. The oligonucleotide primary constructs were designed for amplification and subsequent gene assembly and each consisted of (2) flanking regions, all of which were identical, containing 15 mer primer sites and containing restriction sites (Mly I; GAGTC(N)5 (SEQ ID NO: 1). Each primary construct also included the 40 mer internal regions to be used for subsequent gene assembly. For six of the primary constructs, each half of its internal region was complementary to one half of the internal region of the internal region of another primary construct. Two primary constructs had internal regions that were complementary only for one half of their region to another primary construct internal region.

We included quality control targets on the periphery of this chip to be used to evaluate oligonucleotide synthesis quality. So for this chip, the post-synthesis processing consisted of a 2 hour soak in EDA/EtOH to remove the side-protecting groups from the oligos on the chip, a 2 hour hybridization at 45° C. with the cy3 labeled complement of the QC target, scanning to verify a successful synthesis, removal of the QC labeled probe by denaturing at 75° C. for 30 minutes, and then standard cleavage in $NH_4OH$ for one hour, followed immediately by speedvac dry down (16 our deprotection not necessary as side protecting groups were previously removed in the 2 hour EDA/EtOH soak). The precipitate was subsequently re-suspended in 5 μl sterile Milli-Q water and used for gene assembly.

A chip eluate aliquot (0.3 μl) was used for PCR amplification with two 15 mer PCR primers containing the restriction enzyme site (Mly I). After PCR amplification, the product was digested overnight with Mly I to remove of the flanking regions, leaving the four 40 mer assembly internal regions. The unpurified restriction enzyme digest fragments were then used for subsequent gene assembly and amplification reactions. To perform successful assemblies with increased numbers of oligos, it was noted that increased amounts of the unpurified restriction enzyme digested DNA was needed in the assembly reactions.

Initial gene assembly was performed by combining a fraction of the digested PCR product with Pfu polymerase, buffers, and dNTPs in a reaction vessel, and cycling to denature, anneal and extend the gene fragments. No other primers were added. The assembled sequence was then amplified by PCR with Pfu polymerase, and analyzed by gel electrophoresis on a 3.5% agarose 1×TBE gel. After electrophoresis at 110V for forty-five minutes, the gel was stained with ethidium bromide and analyzed. The gel revealed the expected 180 base pair DNA product.

We claim:

1. A method for making a double-stranded DNA target sequence, the method comprising the following steps in the order set forth below:
   (a) synthesizing in parallel a plurality of single-stranded oligonucleotide primary constructs, each oligonucleotide primary construct comprising:
   (i) an internal region, wherein each internal region has at least one portion overlapping and complementary to a portion of an internal region of at least one different primary construct, and wherein the internal regions of the plurality of oligonucleotide primary constructs together define the double-stranded DNA target sequence, and
   (ii) a 5' and a 3' flanking region flanking the 5' and the 3' end of the internal region, each of the flanking regions including both a primer recognition site and a recognition site for a restriction enzyme capable of cleaving the oligonucleotide primary construct at each of the junctions of the internal region and the flanking regions;

(b) performing polymerase chain reaction (PCR) on the single-stranded primary constructs using a set of PCR primers that target the primer recognition site(s) in the flanking regions to amplify at least a subset of the plurality of the single-stranded oligonucleotide primary constructs of step (a) to generate an amplified pool of double-stranded primary constructs;

(c) cleaving the flanking regions from the double-stranded primary constructs of step (b) by digesting said constructs with the restriction enzyme, thereby generating a plurality of double-stranded internal regions;

(d) denaturing the plurality of double-stranded internal regions of step (c) to form a plurality of single-stranded internal regions;

(e) annealing the complementary portions of two or more different single-stranded internal regions of step (d), thereby producing a plurality of hybridized DNA constructs that include both single-stranded and double stranded segments;

(f) extending the double-stranded segments of the hybridized DNA constructs using a polymerase and dNTPs in the absence of primers, thereby generating a plurality of double-stranded secondary DNA constructs comprising the sequences of two or more of the internal regions of the single-stranded oligonucleotide primary constructs of step (a);

(g) repeating the denaturing, annealing, and extending steps one or more times with the double-stranded secondary DNA constructs produced in the extending step to generate increasingly long double-stranded secondary DNA constructs, whereby the double-stranded DNA target sequence is generated.

2. The method of claim 1 wherein step (a) is performed by using an automated gene synthesizer instrument to construct the primary constructs as single stranded DNA probes in a microarray on a common substrate and by then detaching the primary constructs from the substrate.

3. The method of claim 1 wherein the flanking regions at the ends of all of the primary constructs are the same and wherein in step (b) a single set of PCR primers is used to amplify all of the primary constructs.

4. The method of claim 1 wherein the restriction enzyme used in step (c) is Mly I.

5. The method of claim 1 where step (b) is performed multiple times using multiple different sets of primers.

6. The method of claim 1 wherein the step (c) is performed multiple times using multiple different restriction enzymes.

7. The method of claim 1 wherein for each of the primary constructs except for the two primary constructs corresponding to the two ends of the double-stranded DNA target sequence, each half of the sequence of the internal region of the primary construct is complementary to the sequence of a half of the internal region of another primary construct.

8. The method of claim 1 further comprising the step of isolating from the products of step (g) the longest double-stranded DNA construct produced.

9. The method of claim 1, wherein step (a) of synthesizing in parallel a plurality of single-stranded oligonucleotide primary constructs is performed on a microarray; and wherein for each oligonucleotide primary construct, the oligonucleotide primary construct is at least 70 nucleotides in length, the internal region is at least 40 nucleotides in length, and the flanking regions are at least 15 nucleotides in length.

10. The method of claim 9 wherein step (a) is performed by using an automated gene synthesizer instrument to construct the primary constructs as single stranded DNA probes in a microarray on a common substrate and by then detaching the primary constructs from the substrate.

11. The method of claim 9 wherein the flanking regions at the ends of all of the primary constructs are the same and wherein in step (b) a single set of PCR primers is used to amplify all of the primary constructs.

12. The method of claim 9 wherein the restriction enzyme used in step (c) is Mly I.

13. The method of claim 9 where step (b) is performed multiple times using multiple different sets of primers.

14. The method of claim 9 wherein the step (c) is performed multiple times using multiple different restriction enzymes.

15. The method of claim 9 wherein for each of the primary constructs except for the two primary constructs corresponding to the two ends of the double-stranded DNA target sequence, each half of the sequence of the internal region of the primary construct is complementary to the sequence of a half of the internal region of another primary construct.

16. The method of claim 9 further comprising the step of isolating from the products of step (g) the longest double stranded DNA construct produced.

* * * * *